US010206956B2

(12) United States Patent
Bright et al.

(10) Patent No.: US 10,206,956 B2
(45) Date of Patent: Feb. 19, 2019

(54) COMPOSITIONS AND METHODS FOR REDUCING FREQUENCY AND/OR SEVERITY OF HEADACHE

(71) Applicants: Rusty Property Holdings Pty Ltd, Liverpool (AU); Amberdale Enterprises Pty Ltd, Bar Beach (AU); Tavid Pty Ltd, Merewether (AU)

(72) Inventors: Ralph Bright, Liverpool (AU); Pelin Bright, Liverpool (AU); Bruce Hansen, Liverpool (AU); Wayne Thomas, Liverpool (AU)

(73) Assignees: Rusty Property Holdings Pty Ltd., Liverpool (AU); Amberdale Enterprises Pty Ltd., Bar Beach (AU); Tavid Pty Ltd., Merewether (AU)

( * ) Notice: Subject to any disclaimer, the term of this patent is extended or adjusted under 35 U.S.C. 154(b) by 0 days.

(21) Appl. No.: 14/409,173

(22) PCT Filed: Jun. 26, 2013

(86) PCT No.: PCT/AU2013/000684
§ 371 (c)(1),
(2) Date: Dec. 18, 2014

(87) PCT Pub. No.: WO2014/000029
PCT Pub. Date: Jan. 3, 2014

(65) Prior Publication Data
US 2015/0174172 A1    Jun. 25, 2015

(30) Foreign Application Priority Data

Jun. 26, 2012   (AU) .............................. 2012902720

(51) Int. Cl.
| A61K 35/35 | (2015.01) |
| A61K 35/28 | (2015.01) |
| C12N 5/0775 | (2010.01) |
| A61K 35/16 | (2015.01) |
| A61K 35/19 | (2015.01) |
| A61K 35/32 | (2015.01) |
| A61K 35/50 | (2015.01) |
| A61K 35/51 | (2015.01) |

(52) U.S. Cl.
CPC .............. *A61K 35/35* (2013.01); *A61K 35/16* (2013.01); *A61K 35/19* (2013.01); *A61K 35/28* (2013.01); *A61K 35/32* (2013.01); *A61K 35/50* (2013.01); *A61K 35/51* (2013.01); *C12N 5/0667* (2013.01)

(58) Field of Classification Search
None
See application file for complete search history.

(56) References Cited

U.S. PATENT DOCUMENTS

| 2009/0186007 A1* | 7/2009 | Cordelier ............... | A61K 35/35 |
| | | | 424/93.21 |
| 2012/0101479 A1* | 4/2012 | Paspaliaris ............. | A61K 35/12 |
| | | | 604/522 |
| 2012/0164113 A1* | 6/2012 | Victor .................. | C12N 5/0667 |
| | | | 424/93.7 |
| 2012/0328583 A1* | 12/2012 | Herzberg ............... | A61K 35/50 |
| | | | 424/93.21 |

FOREIGN PATENT DOCUMENTS

| JP | 2010037292 A | 2/2010 |
| JP | 2011010581 A | 1/2011 |
| JP | 2012100662 A | 5/2012 |
| WO | WO-200053795 A1 | 9/2000 |
| WO | WO-2003/039489 A2 | 5/2003 |
| WO | WO-2005013885 A2 | 2/2005 |
| WO | WO-2005/035742 A2 | 4/2005 |
| WO | WO-2010/021715 A1 | 2/2010 |
| WO | WO-2010021714 A2 | 2/2010 |
| WO | WO-2010071862 A1 | 6/2010 |
| WO | WO-2010/127310 A1 | 11/2010 |
| WO | WO-2011/119829 A1 | 9/2011 |
| WO | WO-2011/138786 A2 | 11/2011 |
| WO | WO-2012/083024 A1 | 6/2012 |
| WO | WO-2012/127320 A1 | 9/2012 |

OTHER PUBLICATIONS

Strioga et al., Same or Not the Same? Comparison of Adipose Tissue-Derived Versus Bone Marrow-Derived Mesenchymal Stem and Stromal Cells, Stem Cells and Development, vol. 21, No. 14, 2012.*
Oterino, A., et al. "Analysis of endothelial precursor cells in chronic migraine: A case control study," Cephalagia; 33(4): 236-244 (Nov. 6, 2012).
International Search Report for PCT/AU2013/000684 dated Aug. 30, 2013.
Extended European Search Report issued in corresponding European Application No. 13808616.0, dated Nov. 3, 2015.
Lee et al., "Decreased number and function of endothelial progenitor cells in patients with migraine," Neurology, 70(17):1510-7 (2008).

(Continued)

*Primary Examiner* — Thomas J. Visone
*Assistant Examiner* — Evelyn Y Pyla
(74) *Attorney, Agent, or Firm* — Foley Hoag LLP

(57) ABSTRACT

In one embodiment, the present invention relates to a method for reducing the frequency and/or severity of headache in a subject comprising administering to the subject a composition comprising the stromal vascular fraction or stromal cells of adipose tissue. In another embodiment, the present invention relates to a method for reducing the frequency and/or severity of headache in a subject comprising administering to the subject a composition compositing bone marrow. In another embodiment, the present invention relates to a method for reducing the frequency or severity of headache in a subject comprising administering to the subject a composition comprising adult stem cells.

15 Claims, 2 Drawing Sheets

(56) References Cited

OTHER PUBLICATIONS

Rodriguez-Osorio et al., "Endothelial progenitor cells: A new key for endothelial dysfunction in migraine." Neurology, 79(5):474-9 (2012).
Seaberg et al., "Stem and progenitor cells: The premature desertion of rigorous definitions," Trends Neurosci, 26(3):125-31 (2003).
Zhong et al., "Feasibility investigation of allogeneic endometrial regenerative cells" J Translational Med, 7(1):15 (2009).
Australian Office Action cited during prosecution of AU 2013284338, dated Feb. 23, 2017.
Australian Office Action cited during prosecution of AU 2013284338, dated Jun. 23, 2017.
European Office Action cited during prosecution of EP 13808616.0, dated Apr. 13, 2017.
Japanese Office Action cited during prosecution of JP 2015521630, dated May 1, 2017.

\* cited by examiner

COMPOSITIONS AND METHODS FOR REDUCING FREQUENCY AND/OR SEVERITY OF HEADACHE

CROSS REFERENCE TO RELATED APPLICATIONS

This application is a 371 national stage application of PCT/AU2013/000684, filed Jun. 26, 2013, which claims priority from Australian Provisional Application No 2012902720 filed 26 Jun. 2012, the contents of which are incorporated herein by reference in their entirety.

FIELD OF THE INVENTION

The present invention relates to compositions and methods for reducing the frequency and/or severity of headache.

The invention has been developed primarily for the treatment of migraine, tension headache, trigeminal neuralgia, cluster headache, or headache by administering compositions comprising adult stem cells and will be described hereinafter with reference to this application. However, it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

A headache is a pain in the head, such as in the scalp, face, forehead or neck. A headache can be a primary headache or a secondary headache. A primary headache is a headache which is not caused by another condition. Contrarily, a secondary headache is due to a disease or medical condition, such as an illness, infection, injury, stroke or other abnormality. Thus, with a secondary headache there is an underlying disorder that produces the headache as a symptom of that underlying disorder.

Tension headache is the most common type of primary headache and accounts for about 90% of all headaches. A tension headache is often experienced in the forehead, in the back of the head and neck, or in both regions. It has been described as a tight feeling, as if the head were in a vice. Soreness in the shoulders or neck is common. Nausea is uncommon with a tension headache. Tension-type headaches can be episodic or chronic. Episodic tension-type headaches are defined as tension-type headaches occurring fewer than 15 days a month, whereas chronic tension headaches occur 15 days or more a month for at least 6 months. Tension-type headaches can last from minutes to days, months or even years, though a typical tension headache lasts 4-6 hours.

Migraine headaches are recurrent headaches that may be unilateral or bilateral. Migraine headaches may occur with or without a prodrome. The aura of a migraine may consist of neurologic symptoms, such as dizziness, tinnitus, scotomas, photophobia, or visual scintillations (e.g., bright zigzag lines). Migraines without aura are the most common, accounting for more than 80% of all migraines. An estimated 10-20% of the population suffers from migraine headaches. An estimated 6% of men and 15-17% of women in the United States have migraine. Migraines most commonly are found in women, with a 3:1 female-to-male ratio.

The typical migraine is unilateral (affecting one half of the head) and pulsating in nature and lasting from two to 72 hours. Symptoms include nausea, vomiting, photophobia (increased sensitivity to light) and phonophobia (increased sensitivity to sound).

The cause of migraines is unclear. Migraines vary between people and so does the treatment. Initial treatment is with analgesics for the headache, an antiemetic for the nausea, and the avoidance of triggers.

Preventive migraine drugs are considered effective if they reduce the frequency or severity of migraine attacks by at least 50%. Many medicines are available to prevent or reduce frequency, duration and severity of migraine attacks. Beta blockers, such as Propranolol, atenolol, and metoprolol; calcium channel blockers, such as amLodipine, flunarizine and verapamil; the anticonvulsants sodium valproate, divalproex, gabapentin and topiramate; and tricyclic antidepressants are some of the commonly used drugs. The major problem with migraine preventive drugs, apart from their transient nature and relative inefficacy, is that undesirable side effects are common. Such side effects include insomnia, sedation or sexual dysfunction.

Cluster headache is far less common than migraine headache or tension headache. The cluster headache exhibits a clustering of painful attacks over a period of many weeks. The pain of a cluster headache peaks in about 5 minutes and may last for an hour. Someone with a cluster headache may get several headaches a day for weeks at a time—perhaps months—usually interrupted by a pain-free period of variable length. In contrast to people with migraine headache, perhaps 5-8 times as many men as women have cluster headache. Most people get their first cluster headache at age 25 years, although they may experience their first attacks in their teens to early 50s. There are two types of cluster headache, episodic and chronic. The episodic type is more common and characterised by 2 or 3 headaches a day for about 2 months and then followed by a period of untreated sustained relief for a long period (e.g., a year). The pattern may then repeat. The chronic type behaves similarly to episodic but without the period of untreated sustained relief.

Trigeminal neuralgia is a neuropathic disorder characterized by episodes of intense pain in the face, originating from the trigeminal nerve. The disorder is characterized by episodes of intense facial pain that last from a few seconds to several minutes or hours. The episodes of intense pain may occur paroxysmally. Individual attacks usually affect one side of the face at a time and tend to occur in cycles with remissions lasting months or even years. Certain medicines sometimes help reduce pain and the rate of attacks. These medicines include anti-seizure drugs (carbamazepine, gabapentin, lamotrigine, phenytoin, valproate, and pregabalin), muscle relaxants (baclofen, clonazepam) and tricyclic antidepressants (amitriptyline, nortriptyline, or carbamazepine). Some patients may need surgery to relieve pressure on the nerve. Techniques include cutting or destroying part of the trigeminal nerve, stereotactic radiosurgery or surgery to remove a blood vessel or tumor that is putting pressure on the trigeminal nerve.

About 2% of all headaches are secondary headaches. For example, a cervicogenic headache is a headache which is due to a neck problem, such as an abnormality of neck muscles, which can result from prolonged poor posture, arthritis, injuries of the upper spine, or from a cervical spine disorder. Sinus headache is another type of secondary headache. A sinus headache can be caused by inflammation and/or infection in the paranasal sinuses.

It is an object of the present invention to overcome or ameliorate at least one of the disadvantages of the prior art, or to provide a useful alternative.

SUMMARY OF THE INVENTION

Surprisingly, the present inventors have found that the injection of the stromal vascular fraction or stromal cells of adipose tissue or bone marrow-derived cellular preparations (which all contain adult stem cells) reduce the frequency and/or severity of headache.

In one aspect, the present invention relates to a method of reducing the frequency and/or severity of headache in a subject comprising administering to the subject a composition comprising:

the stromal vascular fraction or stromal cells of adipose tissue; or
a bone marrow-derived cellular preparation.

In another aspect, the stromal vascular fraction or stromal cells of adipose tissue or the bone marrow-derived cellular preparation comprise adult stem cells.

In another aspect, the present invention relates to a method of reducing the frequency and/or severity of headache in a subject comprising administering to the subject a composition comprising adult stem cells.

In another aspect, the adult stem cells are obtained from adipose tissue, bone marrow or blood.

In another aspect, the adult stem cells are mesenchymal stem cells and/or early mesenchymal/stromal precursor cells, and/or adipose-derived stromal/stem cells and/or bone marrow stomal/stem cells.

In another aspect, the headache is selected from the group consisting of migraine, tension headache, trigeminal neuralgia and cluster headache.

In another aspect, the adipose tissue, bone marrow or stem cells are autologous or allogeneic.

In another aspect, the adipose tissue is lipoaspirate.

In another aspect, the lipoaspirate is abdominal lipoaspirate.

In another aspect, adipose tissue is treated with an enzyme and/or dissociating reagent, such as collagenase or lecithin, to break up the tissue.

In another aspect, the adipose tissue is subjected to mechanical agitation to break up the tissue.

In another aspect, the adipose tissue is treated with ultrasonic cavitation to lyse adipocytes, separate out the stromal/stem cells and/or separate out extracellular matrix.

In another aspect, the stromal vascular fraction or stromal cells of adipose tissue, bone marrow-derived cellular preparations or adult stromal/stem cells are treated with stem cell activators, such as platelet-rich plasma, plasma rich in growth factors, LED or low-level laser or others.

In another aspect, the stromal vascular fraction or stromal cells of adipose tissue, bone marrow-derived cellular preparations or adult stromal/stem cells are administrated to the subject intravenously, subcutaneously, intra-muscularly or intra-articularly, or added to fat for fat transfer.

In another aspect, the present invention relates to a method of reducing the frequency and/or severity of headache in a subject comprising administering to the subject a composition comprising stem cells obtained from umbilical cord (Wharton's jelly), umbilical cord blood or placenta. Such stem cells may be allogeneic and optionally treated with platelet-rich plasma or other stem cell activators, such as LED or low-level laser.

In another aspect, the present invention relates to a method of reducing the frequency and/or severity of headache in a subject comprising administering to the subject a composition comprising adipose-derived and/or stromal-derived extra-cellular matrix.

In another aspect, the present invention relates to use of a composition comprising:

the stromal vascular fraction or stromal cells of adipose tissue; or
a bone marrow-derived cellular preparation, for the manufacture of a medicament for reducing the frequency and/or severity of headache.

In another aspect, the present invention relates to use of a composition comprising adult stem cells for the manufacture of a medicament for reducing the frequency and/or severity of headache.

In another aspect, the present invention relates to use of a composition comprising stem cells obtained from umbilical cord (Wharton's jelly), umbilical cord blood or placenta for the manufacture of a medicament for reducing the frequency and/or severity of headache. Such stem cells may be allogeneic and optionally treated with platelet-rich plasma or other stem cell activators, such as LED or low-level laser.

In another aspect, the present invention relates to use of a composition comprising adipose tissue-derived and/or stromal-derived extra-cellular matrix for the manufacture of a medicament for reducing the frequency and/or severity of headache.

In another aspect, the present invention relates to a composition comprising:

the stromal vascular fraction or stromal cells of adipose tissue; or
a bone marrow-derived cellular preparation, for use in reducing the frequency and/or severity of headache.

In another aspect, the present invention relates to a composition comprising adult stem cells for use in reducing the frequency and/or severity of headache.

In another aspect, the present invention relates to a composition comprising stem cells obtained from umbilical cord (Wharton's jelly), umbilical cord blood or placenta for use in reducing the frequency and/or severity of headache.

In another aspect, the present invention relates to a composition comprising adipose tissue-derived and/or stromal-derived extra-cellular matrix for use in reducing the frequency and/or severity of headache.

As used herein, the term "adipose tissue" refers to any fat tissue. The adipose tissue may be brown or white adipose tissue. The adipose tissue may be mesenchymal or stromal. Preferably, the adipose tissue is subcutaneous white adipose tissue. The adipose tissue may be from any organism having fat tissue. Preferably the adipose tissue is mammalian, most preferably the adipose tissue is human. A convenient source of human adipose tissue is that derived from liposuction surgery or other surgery. However, the source of adipose tissue or the method of isolation of adipose tissue is not critical to the invention.

As used herein the term "stromal vascular fraction" refers to a fraction, comprising cells, derived from blood vessels and surrounding tissue found in adipose tissue or bone marrow. The fraction may comprise different cell types including, by way of example, mesenchymal stem cells, early mesenchymal/stromal precursor cells, adipose-derived stromal stem cells, Muse-AT cells, hematopoietic cells, hematopoietic stem cells, platelets, Kupffer cells, osteoclasts, megakaryocytes, granulocytes, NK cells, endothelial precursor or progenitor cells, progenitor cells, CD34+ cells, Stro-1+ cells, Stro-3+ cells, CD29+ cells, CD166+ cells, Thy-1+ or CD90+ stem cells, CD44+ cells, immune cells such as monocytes, leukocytes, lymphocytes, BandT cells, NK cells, macrophages, neutrophil leukocytes, neutrophils, neutrophil granulocytes, and the like. The stromal vascular fraction also includes cells expressing any of the markers or any combination thereof disclosed herein. As used herein, the term "stromal vascular fraction" includes within its scope terms such as "mesenchymal vascular fraction", "mesenchymal fraction", "stromal fraction", "pre-mesenchymal fraction", "mesenchymal progenitor" and the like As used herein, the term "adult stem cell" refers to undifferentiated cells found throughout the body after embryonic development in children and adults that divide to replenish dying cells and regenerate damaged tissues. As used herein, the term "adult stem cell" excludes cells obtained from a foetus or an embryo.

As used herein, the term "differentiated" refers to a cell that has achieved a terminal state of maturation such that the cell has developed fully and demonstrates biological specialization and/or adaptation to a specific environment and/or function. Typically, a differentiated cell is characterized by expression of genes that encode differentiation-associated proteins in that cell. For example expression of GALC in a leukocyte is a typical example of a terminally differentiated leukocyte.

As used herein, the term "mesenchymal stem cell" refers to stromal or mesenchymal cells or early mesenchymal/stromal precursor cells or adipose tissue-derived stromal/stem cells which are multipotent and can serve as stem cell-like precursors to a variety of different cell types such as but not limited to adipocytes, osteocytes, chondrocytes, muscle and neuronal/glial cell lineages. Mesenchymal stem cells make up a subset population derivable from, for example, adipose tissue and bone marrow. As used herein, the term "mesenchymal stem cell" includes within its scope terms such as "stromal stem cell", "marrow stromal cell", "multipotent stromal cell", "mesenchymal precursor cell" and the like.

The terms "precursor cell", "progenitor cell", and "stem cell" are used interchangeably in the art and herein and refer either to a pluripotent, or lineage-uncommitted, progenitor cell, which is potentially capable of an unlimited number of mitotic divisions to either renew itself or to produce progeny cells which will differentiate into the desired cell type. In contrast to pluripotent stem cells, lineage-committed progenitor cells are generally considered to be incapable of giving rise to numerous cell types that phenotypically differ from each other. Instead, progenitor cells give rise to one or possibly two lineage-committed cell types.

As used herein, the term "multipotent", "multipotential" or "multipotentiality" is meant to refer to the capability of a stem cell to differentiate into more than one type of cell.

As used herein, the term "allogeneic" is meant to refer to any material derived from a different mammal of the same species.

As used herein, the term "autologous" is meant to refer to any material derived from an individual and re-introduced to the individual.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

DETAILED DESCRIPTION OF THE PREFERRED EMBODIMENT

Figure 1:
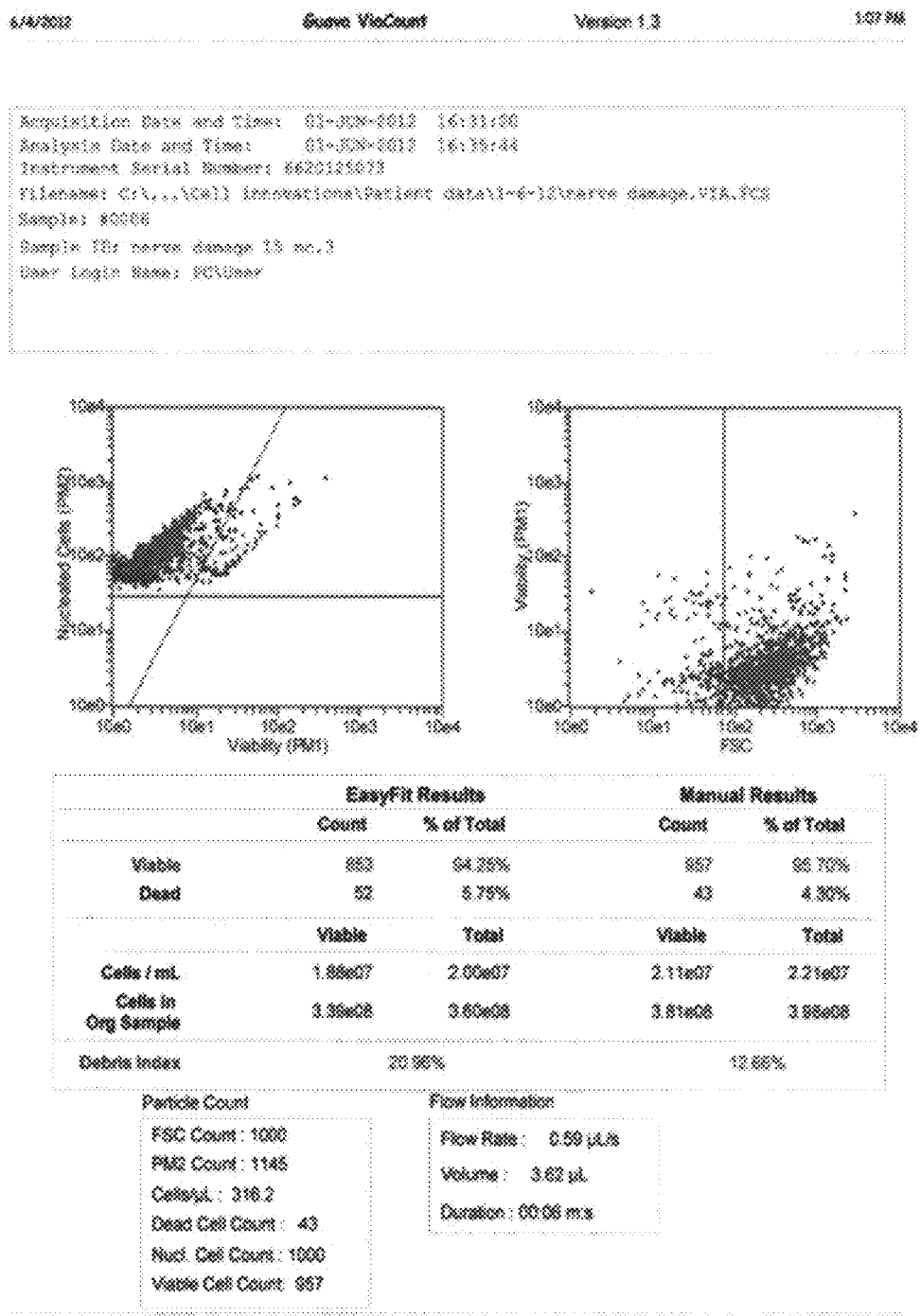
FIG. 1: FACS analysis of cells obtained from ultrasonic cavitation treated adipose tissue—cell count by fluorescent nuclei of 40 grams of adipose tissue separated by ultrasonic cavitation

This invention is based on the surprising finding that the injection of the stromal vascular fraction or stromal cells of adipose tissue or bone marrow-derived cellular preparations (which all contain adult stem cells) reduces the frequency and severity of migraine.

The adipose tissue may be obtained via liposuction surgery, aspiration of fat or isolated by other surgical methods. The donor will preferably be the same patient who is to be treated with the stromal vascular fraction or mesenchymal stem cells or will be an allogeneic donor that is immune compatible with the treated individual. Those of ordinary skill in the art can readily identify matched donors using standard techniques and criteria.

Adipose tissue may be harvested using standard liposuction techniques and the stromal vascular fraction separated from the adipose tissue by means of ultrasonic cavitation and/or enzyme treatment and/or mechanical agitation.

In one embodiment, the method of the invention uses an ultrasonic cavitation device having a probe that is placed into contact with the adipose tissue so as to explode or lyse most of the fat cells in the adipose tissue and release the stromal vascular fraction. The particular ultrasonic cavitation device used is not critical to the invention. One suitable selection is the HIELSCHLER ultrasonic processors which is a technologically advanced high intensity ultrasonic processor. This device can safely process a wide range of organic and inorganic materials—from microliters to liters. Other devices which may be used include Vibra-Cell™ device (Sonics), VASER (SoltaMedical) or QSonica ultrasonic processors.

In another embodiment, adipose tissue in a biologic solution (e.g., phosphate buffered saline solution or normal saline solution) may be placed into a chilled environment (the tissue/cells should not fall below 2° C.). An ultrasonic cavitation device probe is placed into the adipose tissue and the amplitude is set at about 20%, about 30%, about 40%, about 50%, about 60%, about 70%, about 80%, cycle at about 0.2, about 0.3, about 0.4, about 0.5, about 0.6, about 0.7, about 0.8, about 0.9, for about 10 seconds, about 20 seconds, about 30 seconds, about 40 seconds, about 50 seconds, about 60 seconds, about 1 minute 10 seconds, about 1 minute 20 seconds, about 1 minute 30 seconds, about 1 minute 40 seconds, about 1 minute 50 seconds, about 2 minutes, about 3 minutes, about 4 minutes, about 5 minutes, about 6 minutes, about 7 minutes, about 8 minutes, about 9 minutes, about 10 minutes. The probe may be adjusted in at different positions in the tube during the operation. The procedure may occur at room temperature and the amplitude, cycle and time adjusted to prevent the temperature of the adipose tissue rising above about 43° C. to about 45° C. The sequence and timing of ultrasonic cavitation (specifically, the amplitude, cycles and time of application) may vary but is determined to the extent of ensuring the optimal cell numbers and viability of the stem cells in the stromal vascular fraction by preventing the adipose tissue temperature from rising above ideally 37° C. or no more than about 43° C. to about 45° C. These parameters can be easily determined by simple trial and error. Typically, the amplitude is about 50%, the cycle is about 0.4 to about 0.5 and the time is about one minute and 30 seconds. If amplitude is increased, the cycle or time can be consequently decreased (or vice versa) to ensure that the temperature of the adipose tissue does not rise above about 43° C. to about 45° C. After ultrasonication there is a thick solution in the tube (which cannot be filtered or easily separated into the stromal vascular fraction) and may be centrifuged.

Centrifugation results in 3 layers—the top lipid layer, the middle floating layer containing extracellular matrix and stromal vascular cells, and a bottom layer of fluid. The top lipid layer must be removed and discarded and the remaining contents of the tube mixed well to separate the extracellular matrix and 0.9% normal saline added. Further centrifugation brings about the cells and extra-cellular matrix to fall out and pellet at the bottom—the pellet contains extracellular matrix and stromal vascular fraction comprising viable and functional stem cells (including mesenchymal stem cells). The pellet may be filtered to remove any large debris.

In another embodiment, the present invention relates to recovering a stromal vascular fraction or stromal cells from adipose tissue, the method comprising treating the adipose tissue with ultrasonic cavitation for a time, amplitude and cycle that maintains the viability of adult stem cells within the stromal vascular fraction.

In another embodiment, the adipose tissue is treated with ultrasonic cavitation for a period of about 10 seconds to about 10 min with an ultrasonic device set at amplitude about 20% to about 75% and cycle about 0.2 to about 0.9.

In another embodiment, the temperature of the adipose tissue does not exceed about 43° C.

In another embodiment, the method of the invention uses an enzyme, such as collagenase, and agitation to produce an adipose-derived cell suspension which is centrifuged and washed to separate the stromal vascular fraction or stromal cells.

In another embodiment, the method of the invention uses lecithin, and agitation to produce an adipose-derived cell suspension which is centrifuged and washed to separate the stromal vascular fraction or stromal cells.

The stromal vascular fraction or stromal cells of adipose tissue, bone marrow-derived cellular preparations or adult stem cells may be directly infused in subjects in need thereof by traditional administration routes, such as intravenous injection, or they can be further processed to purify (and expand in culture if desired) desired cell types such as mesenchymal stem cells, STRO-1+ cells, STRO-3+ cells, adipose-derived stromal stem cells, mesenchymal precursor cells or Muse-AT cells prior to administration.

In some embodiments, mesenchymal stem cells can be isolated, purified or enriched from the stromal vascular fraction or stromal cells of adipose tissue or bone marrow-derived cellular preparations by fractionation using unique cell surface antigens and fluorescence activated call sorting (FACS) for expansion in vitro.

In other embodiments, the stromal vascular fraction or stromal cells of adipose tissue, bone marrow-derived cellular preparations or adult stem cells may be cultured, expanded and/or differentiated prior to administration.

In other embodiments, the stromal vascular fraction or stromal cells of adipose tissue, bone marrow-derived cellular preparations or adult stem cells may be stored for later implantation/infusion. Moderate to long-term storage in a cell bank is also within the scope of this invention.

At the end of processing, the stromal vascular fraction or stromal cells of adipose tissue, bone marrow-derived cellular preparations or adult stem cells may be loaded into a delivery device, such as a syringe or IV bag, for administration to the recipient by either subcutaneous, intra-articular, intravenous, intramuscular, or intraperitoneal techniques. In other words, cells may be placed into the patient by any means known to persons of ordinary skill in the art, for example, they may be injected into blood vessels for systemic or local delivery, into tissue (e.g., cardiac muscle, or skeletal muscle), into joints (intra-articular), into the dermis (subcutaneous), into tissue space (e.g., pericardium or peritoneum), or into tissues (e.g., periurethral emplacement), or other location. Preferred embodiments include placement by needle or catheter, or by direct surgical implantation in association with additives such as a pre-formed matrix or adipose-derived or stromal-derived extra-cellular matrix.

The stromal vascular fraction or stromal cells of adipose tissue, bone marrow-derived cellular preparations or adult stem cells may be applied alone or in combination with other cells, tissue, tissue fragments, demineralized bone, growth factors such as insulin or drugs such as members of the thiaglitazone family, biologically active or inert compounds, resorbable plastic scaffolds, adipose-derived or stromal-derived lattice and/or extra cellular matrix or other additive intended to enhance the delivery, efficacy, tolerability, or function of the cell population. In certain embodiments of the invention, the cells are administered to a patient with one or more cellular differentiation agents, such as cytokines and growth factors. In other embodiments, the cells are treated with platelet-rich plasma or plasma rich in growth factors.

The present invention will now be described in more detail with reference to specific but non-limiting examples describing specific compositions and methods of use. It is to be understood, however, that the detailed description of specific procedures, compositions and methods is included solely for the purpose of exemplifying the present invention. It should not be understood in any way as a restriction on the broad description of the inventive concept as set out above.

EXAMPLES

Example 1—Preparation of Adipose Tissue by Liposuction

An excess amount of Tumescent solution (containing, in one liter of normal saline, 1 mg adrenalin, 800 mg lignocaine and 10 mLs of a 8.4% sodium bicarbonate solution), which exceeds the amount of liposuction to be aspirated prior to the liposuction operation, was infused into hypodermic fat layer (tumescent method), and thereafter cannulae having, for example, 2-3 mm of inner diameter (made of metal with aspirator) was used for the liposuction operation. Liposuction operations are well known in the art, and for example, can be referred to in Biyo Seikei Shujutsu Practice 2 (Cosmetic Operation Practice 2), ed. Masanari ICHIDA, Ryusaburo TANINO, and Yoshiaki HOSAKA, published by BUNKODO, pp. 429-469, which is incorporated herein by reference in its entirety.

Aspirated fat was washed with saline. About 50 ml to ten liters of washed aspirate may be generated, and the resultant adipose tissue derived cellular materials used for derivation of stromal vascular fractions.

Example 2—Preparation of Adipose Tissue by Surgery

Fat tissue was obtained by surgery from human subjects who had given their informed consent. Separation was conducted with techniques well known in the art. Briefly, human fat tissue was aseptically separated from fat tissue suctioned from human subjects who had given their informed consent. The resultant adipose tissue derived cellular materials are used for derivation of stromal vascular fractions.

Example 3—Preparation of Platelet-Rich Plasma and Plasma Rich Growth Factors

1) Blood is collected prior to anaesthetic. 2×9 mL acid citrate dextrose (ACD-A) blood collection tubes (BD vacutainer) are filled (vacuum pressure). The blood is drawn using an 18 G needle or larger to avoid activating the platelets by shearing. The contents of the blood tubes are mixed by inverting the tubes 3-4 times.
2) The ACD-A blood filled tubes are centrifuged at 450 g×10 min.
3) The plasma layer (the top layer) is removed from each tube with the same transfer pipette and placed into a 15 mL sterile tube. The blood should not be disturbed and the thin layer of white cells resting on the blood should be avoided. It is best to leave a 5 mm layer of plasma above the red blood cells. This plasma containing enriched platelets (PRP) can be used as is or further treated as below.
4) The tube containing the plasma is centrifuged for 2000 g/10 min—a small pellet of platelets at the bottom of the tube should form.
5) The top platelet poor plasma should be removed with a transfer pipette down to 1.5 mL and discarded. The pellet should be resuspended in the remaining 1.5 mL using the same transfer pipette. This is the platelet-rich plasma (PRP).
6) PRP may be used as is or if desired clotted with 150 µl of the calcium gluconate (1 mL syringe and needle) added to the PRP and mixed well. The tube should be placed in a water bath (37° C.—without shaking) or left at room temperature for longer period of time. The PRP should form a solid gel.
7) After solidification, the PRP can be left at either 37° C. (to speed up the process) or room temperature to partially dissolve over the next 1-2 hr—this is known as plasma rich growth factors (PRGF).

Example 4—Preparation of the Stromal Vascular Fraction of Adipose Tissue by Collagenase and/or Lecithin Treatment 1) Between 50-1000 mL of lipoaspirate was obtained from the patient's abdomen using a 3 mm cannula and Modified Klein's solution (containing, in one liter of normal saline, 1 mg adrenalin, 400 mg to 800 mg lignocaine and 10 mLs of a 8.4% sodium bicarbonate solution). The lipoaspirate was rinsed with normal saline and placed in 500 mL centrifuge pots.
2) Collagenase (Serva) is added to achieve a final concentration of 0.05% (filter sterilized through a 0.22 µm sterile filter) and/or lecithin 10% (Adistem).
3) The sample was incubated at 37° C. for 30-90 minutes in a water bath (37° C.), and gently agitated. During the incubation the sample is gently inverted by hand every 15 minutes.
4) Following incubation the sample was centrifuged at 500 g×5 min. Three layers were present after the centrifugation. The top yellow/clear layer (lipid layer). The white fibrous middle layer and, the red/white bottom layer which has a cell pellet at the bottom of the tube.
5) The cell pellets are removed from the pots by drawing up the pellet with a mixing cannula and syringe.
6) The cell pellets are expelled into a 50 mL centrifuge tube and PBS added to 40 mL. The tube contents are aseptically filtered through a 100 µm steriflip (Millipore) using a vacuum pump into the 50 mL tube.
7) The filtrate is centrifuged at 500 g for 5 minutes.
8) The supernatant is removed without disturbing the pellet and all cell pellets combined into the one centrifuge tube. The resultant pellet is resuspended and 40 mL PBS added.
9) The cell suspension is centrifuged at 500 g for 5 minutes and the supernatant removed.
10) 20 mL PBS is added and the cell suspension filtered through a 60 µm steriflip (Millipore).
11) The filtrate is centrifuged at 500 g for 5 minutes and the supernatant removed. A sample is removed for cell counting (a sample of 50 µl of well mixed cells is added to 0.4% of trypan blue, mixed and allowed to stand for 1-2 minutes before placing the sample into a chamber of the haemocytometer. Cell count and viability is determined by counting at least 100 cells in the grid area. Viable cells are determined by exclusion of trypan blue).
12) 5-10 mL PRP or PRGF may be added or normal saline.
13) The sample is drawn up into a syringe and injected into normal saline IV 1 liter bag for infusion into the patient Example 5—Preparation of the Stromal Vascular Fraction of Adipose Tissue by Ultrasonic Cavitation 1) Adipose tissue derived from liposuction aspirates or surgically as described in the examples 1 or 2 were placed in a suitable tube and a biologic solution (e.g., phosphate buffered saline solution or normal saline solution).
2) Excess fluid was removed by either draining through the end of the syringe or the tube was centrifuged at 200 g/2 minutes to separate out the excess fluid and adipose tissue. The excess fluid at the base of the tube is removed.
3) (optional) The tube is placed into a chilled environment and care taken to ensure that the temperature of the tissue/cells does not fall below 2° C.
4) The ultrasonic cavitation device probe is placed into the adipose tissue and the amplitude is set at 50%, cycle 0.4 to 0.5. The probe is raised and lowered for 1 minute and then for about 30-40 seconds at one or two different locations in the tube (i.e., bottom and top of the tube). The process is optionally repeated after 3 minutes.
5) Care was taken to ensure that the adipose tissue temperature did not rise above ideally 37° C. or at most no more than about 43° C.
6) After ultrasonication a thick solution is observed in the tube and is centrifuged at 800 g/5 min.
7) After centrifugation there are 3 layers—the top lipid layer, the middle floating layer containing extracellular matrix and stromal vascular cells, and a bottom layer of fluid.
8) The top lipid layer is removed and discarded using a mixing cannula and syringe and the remaining contents of the tube mixed well to further disrupt the extra-cellular matrix.
9) An isotonic solution (normal saline) is added to the tube to 45 ml and the tube centrifuged at 800 g/5 mins initiating the cells and extra-cellular matrix to fall out and pellet at the bottom.
10) A large pellet is observed at the bottom of tube containing extracellular matrix and the stromal vascular fraction comprising viable and functional stem cells. The pellet is then removed using a mixing cannula and syringe and filtered through a 100 µm filter to remove any large debris.

11) A sample is removed for cell counting—typical cell numbers derived from 20 g of adipose tissue using this method are between about 40 to about 200×10$^6$ i.e., about 2 to about 10×10$^6$/gram, which is greater than that from collagenase separation which typically results in about 0.5× 10$^6$/gram of adipose tissue.

12) PRP, PRGF or other cellular growth factors/cytokines may be added to the cell pellet prior to injection or at the time of injection.

13) The sample was drawn up into a syringe and injected intra-articular, intra-muscular, or intra peritoneal or into normal saline IV 1 liter bag for infusion, into the patient.

Figure 2:
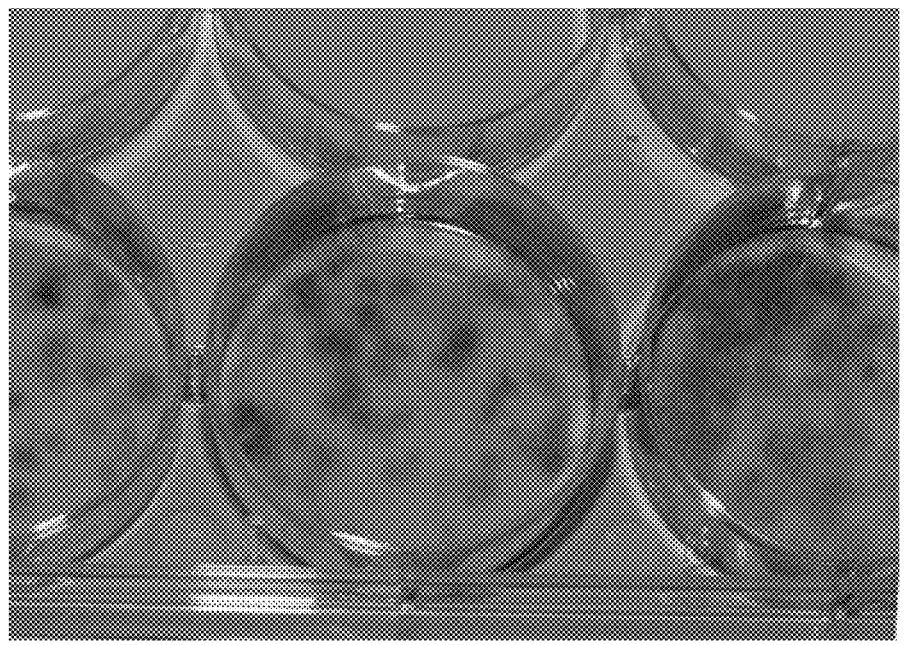
FIG. 2: Giemsa stained colonies of cells grown from ultrasonic cavitation treated adipose tissue.
Figure 3:
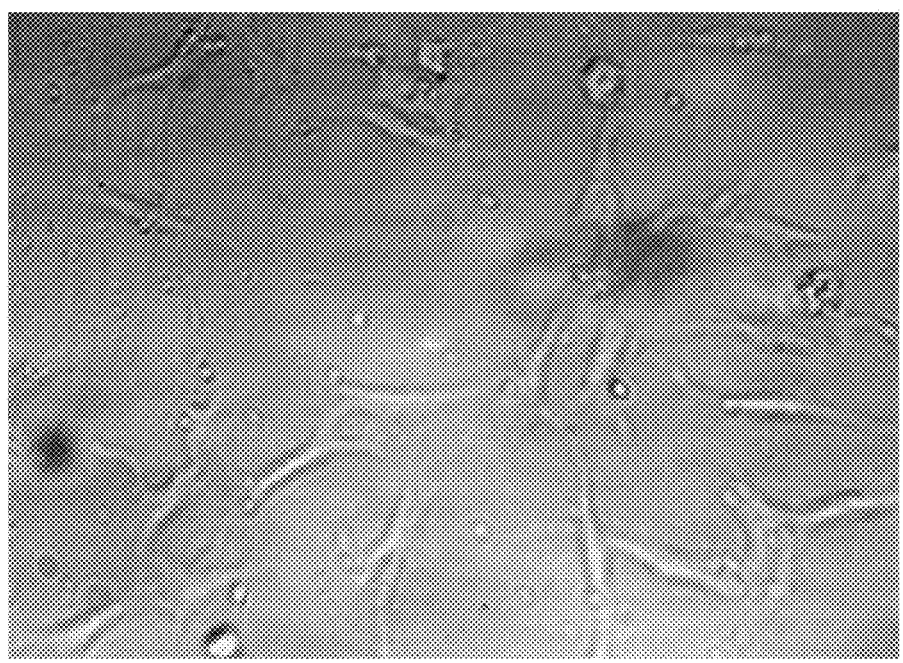
FIG. 3: Cell culture of mesenchymal stem cells grown from ultrasonic cavitation treated adipose tissue.

Analysis of the cell pellet showed the presence of viable cells (FIG. 1) that can be grown in culture (see Example 7 and FIG. 2) and contains mesenchymal stem cells (FIG. 3).

Example 6—Preparation of Bone Marrow

Bone marrow is extracted from the sternum, posterior ilium, or anterior ilium. The site is prepared with Betadine solution and local anesthesia is placed under the skin. A longer needle is used to identify the midpoint of the iliac crest and deposit 3-4 mL 2% Xylocaine under the periosteum. A "J" needle is inserted into the anterior/posterior iliac wing. The needle is rotated gently into 1 cm of the marrow cavity. The stylet is removed from the needle and a 5-cc syringe attached. Bone marrow is aspirated by refraction of the plunger of the syringe. After 2-3 mL of marrow is collected, the needle can be repositioned if more marrow can be obtained Bone marrow cells harvested either by the perfusion or aspiration method are centrifuged and suspended in 15 mL of PBS. They are placed on 15 mL of a (1.077 g/mL) density solution (Lymphoprep). After centrifugation for 30 minutes at 2,000 rpm at room temperature, the bone marrow cells are collected from the defined layer at the interface.

Example 7—Preparation of Expanded Mesenchymal Stem Cells

Adult stem cell can be obtained from adipose tissue by any suitable method and cultured without differentiation using standard cell culture medium (e.g., alphaMEM (Gibco) supplemented with 10% foetal calf serum or human serum, or serum free medium (Gibco)). Primary cultures are plated at 1×10$^6$/100 mm. Preferably the cells are expanded for 1-2 passages but can be passaged up to 7 times in 5% $CO_2$ or hypoxic environment. Such cells can be clonally passaged if required. The isolated cells, autologous or allogeneic, are cultured to a suitable point, generally 2 passages, and viability and yield assessed by standard methods. Standard testing of expanded cells occurs by positive stem cell markers CD29+, CD44+, CD90+, CD105+. The isolated cells can be differentiated into cartilage, bone and adipose cells—demonstrating their potential to differentiate into cells of different tissues. Regarding Good Medical Practice procedures, besides standard serological tests on hepatitis, HIV and treponema, there are PCR tests on 16s subunits for bacteria and fungi, dapi staining for mycoplasma, impurities and cell viability, and evaluation of microscopical morphology before cryopreservation. The above-mentioned PCR tests and testing for endotoxins/pyrogens with Limulus Amoebocyte Lysate (LAL) may be performed before application.

Example 8—Administration of the Stromal Vascular Fraction or Stromal Cells of Adipose Tissue to Patients with History of Migraine Patient 1

This patient has long history of migraines and headaches satisfying the international classification of Headache Disorders 2nd Edition 1st Revision 1.5.1 Chronic Migraine, i.e., patient typically suffered more than 20 days/month of migraines. Mixed tension and migraine no aura present.

After a single IV administration of adipose tissue-derived stromal vascular fraction (546 million cells from 700 mL adipose tissue) prepared according to Example 5 (with addition of PRGF), the patient had only one headache 1 month later.

Patient 2

This patient has a long history of migraines/headaches satisfying the international classification of Headache Disorders 2nd Edition 1st Revision 1.5.1 Chronic Migraine, i.e., patient typically suffered more than 20 days/month of migraines. The patient wore a morphine patch, paracetamol and codeine phosphate up to 8 tablets a day, or oxycodone hydrochloride.

After a single IV administration of adipose tissue-derived stromal vascular fraction (495 million cells from 1,005 mL adipose tissue) prepared according to Example 4 (collagenase), the patient recorded one migraine and some minor headaches in a 5 month period. Results were noticed after 3 days of treatment and morphine patches were discontinued. Minor headaches returned after 5 months and patient was re-treated at 7 months with 638 million cells IV prepared according to Example 4. Improvements were seen from day 1. Paracetamol dosage is reduced to once a week. At 18 months only 7 migraines and some normal headaches were experienced.

Patient 3

This patient has a long history of migraine and tension headaches satisfying the International Classification of headache Disorders 2nd Edition 1st revision 1.2.1 Typical Aura with Migraine headache and 2.2 Frequent episodic tension-type headache. This patient has a life long history of headaches, Typically 2 migraines a day with typical aura and frequent eposidic tension type headaches.

After a single IV administration of adipose tissue-derived stromal vascular fraction (2.93 billion cells) prepared according to Example 4 (collagenase and Lecithin) and Example 5 (with addition of PRGF).

Results were noticed after 3 days of treatment. At 1 month stopped all headache medication. At 3 months only 1 tension headache. By 4 months the occasional mild tension headache Patient 4

This patient has long history of migraines and headaches satisfying the international classification of Headache Disorders 2nd Edition 1st Revision 1.5.1 Chronic Migraine, i.e., patient typically suffered more than 20 days/month of migraines.

After a single IV administration of adipose tissue-derived stromal vascular fraction (41 million cells) prepared according to Example 5, the patient over the last 12 months had only 2 bad headaches, 3 weeks apart about 2 months ago (not as severe as a migraine but did have bad sinuses concurrent with the migraines) No migraines in the past year. In the past needed a home visit from the doctor for a injection to alleviate the pain. Patient is now only taking paracetamol occasionally.

The claims defining the invention are as follow:

1. A method of reducing the frequency of migraine and/or tension headache, and/or the severity of recurrent migraine and/or tension headache, in a subject in need thereof comprising administering intravenously to the subject a composition comprising:

the stromal vascular fraction or stromal cells of adipose tissue; or a bone marrow-derived preparation of cells, wherein the stromal vascular fraction or stromal cells of adipose tissue or the bone marrow-derived preparation of cells comprises adult stem cells, wherein the adult stem cells are mesenchymal stem cells and/or early mesenchymal/stromal precursor cells, and/or adipose issue-derived stromal/stem cells.

2. The method according to claim 1 wherein the adipose tissue or bone marrow is autologous.

3. The method according to claim 1 wherein the adipose tissue or bone marrow is allogeneic.

4. The method according to claim 1 wherein the adipose tissue is treated with an enzyme and/or dissociating reagent.

5. The method according to claim 4 wherein the enzyme is collagenase and the dissociating reagent is lecithin.

6. The method according to claim 1 wherein the adipose tissue is subjected to ultrasonic cavitation.

7. The method according to claim 6 wherein the ultrasonic cavitation lyses adipocytes.

8. The method according to claim 1 wherein the adipose tissue is subjected to mechanical agitation.

9. The method according to claim 1 wherein the stromal vascular fraction or stromal cells of adipose tissue or the bone marrow-derived preparation of cells is treated with platelet-rich plasma or plasma rich in growth factors.

10. A method of reducing the frequency of migraine and/or tension headache, and/or the severity of recurrent migraine and/or tension headache, in a subject in need thereof comprising administering intravenously to the subject a composition comprising adult stem cells, wherein the adult stem cells are mesenchymal stem cells and/or early mesenchymal/stromal precursor cells and/or adipose tissue-derived stromal/stem cells.

11. The method according to claim 1 or claim 10 the adult stem cells have been expanded and/or cultured.

12. The method according to claim 10, wherein the mesenchymal stem cells and/or early mesenchymal/stromal precursor cells are obtained from adipose tissue, bone marrow or blood.

13. The method according to claim 10 wherein the adult stem cells are autologous.

14. The method according to claim 10 wherein the adult stem cells are allogeneic.

15. The method according to claim 10 wherein the adult stem cells are treated with platelet-rich plasma or plasma rich in growth factors.

* * * * *